(12) United States Patent
Sethumadhavan et al.

(10) Patent No.: US 10,061,894 B2
(45) Date of Patent: Aug. 28, 2018

(54) SYSTEMS AND METHODS FOR MEDICAL REFERRAL ANALYTICS

(71) Applicant: Apixio, Inc., San Mateo, CA (US)

(72) Inventors: Vishnuvyas Sethumadhavan, Mountain View, CA (US); Shahram Shawn Dastmalchi, San Ramon, CA (US); Darren Matthew Schulte, San Francisco, CA (US); Robert Derward Rogers, Pleasanton, CA (US); John O. Schneider, Los Gatos, CA (US); Imran N. Chaudhri, Potomac, MD (US)

(73) Assignee: APIXIO, INC., San Mateo, CA (US)

( * ) Notice: Subject to any disclaimer, the term of this patent is extended or adjusted under 35 U.S.C. 154(b) by 351 days.

(21) Appl. No.: 14/245,986

(22) Filed: Apr. 4, 2014

(65) Prior Publication Data

US 2014/0304003 A1    Oct. 9, 2014

Related U.S. Application Data

(63) Continuation-in-part of application No. 13/798,031, filed on Mar. 12, 2013, which is a (Continued)

(51) Int. Cl.
*G16H 40/20* (2018.01)
*G06F 19/00* (2018.01)
(Continued)

(52) U.S. Cl.
CPC .......... *G06F 19/327* (2013.01); *G06F 19/328* (2013.01); *G06F 21/6245* (2013.01); *G06Q 50/24* (2013.01); *G16H 40/20* (2018.01)

(58) Field of Classification Search
CPC .. G06F 19/327; G06F 19/328; G06F 21/6245; G16H 40/20; G06Q 50/24
See application file for complete search history.

(56) References Cited

U.S. PATENT DOCUMENTS 7,321,861 B1    1/2008   Oon
7,702,524 B1    4/2010   Whibbs et al.
(Continued)

FOREIGN PATENT DOCUMENTS

KR    10-2009-0050881    5/2009

OTHER PUBLICATIONS

ISA/US, "Notification of Transmittal of the International Search Report and the Written Opinion of the International Searching, or the Declaration" Authority for PCT application No. PCT/US2014/012138, dated Apr. 21, 2014, 7 pages.
(Continued)

*Primary Examiner* — Linh Giang Le
(74) *Attorney, Agent, or Firm* — Kang S. Lim

(57) ABSTRACT

A health information management system is provided which includes the ability to identify explicit referral activity reported into a referral workflow system, infer referral activity not reported into the referral workflow system utilizing intent-based clustering of medical information, and generate reporting metrics from the inferred and explicit referral activity. Additionally, a referral suggestion may be generated for an identified condition. Physicians are selected within a geographic area who are properly specialized for the condition. This group is then filtered based upon patient preferences and default preferences in order to generate physician referrals.

14 Claims, 20 Drawing Sheets

Related U.S. Application Data continuation-in-part of application No. 13/223,228, filed on Aug. 31, 2011.

(60) Provisional application No. 61/754,527, filed on Jan. 18, 2013, provisional application No. 61/379,228, filed on Sep. 1, 2010.

(51) Int. Cl.
*G06Q 50/24* (2012.01)
*G06F 21/62* (2013.01)

(56) References Cited

U.S. PATENT DOCUMENTS

| | | |
|---|---|---|
| 2005/0138017 A1 | 6/2005 | Keen et al. |
| 2006/0036619 A1 | 2/2006 | Fuerst et al. |
| 2006/0047669 A1 | 3/2006 | Durrence et al. |
| 2006/0129435 A1 | 6/2006 | Smitherman et al. |
| 2006/0265253 A1* | 11/2006 | Rao ................. G06F 19/321 705/3 |
| 2007/0016450 A1 | 1/2007 | Bhora et al. |
| 2008/0091633 A1 | 4/2008 | Rappaport et al. |
| 2008/0263048 A1 | 10/2008 | Wise |
| 2008/0270340 A1 | 10/2008 | Abrams et al. |
| 2009/0024615 A1 | 1/2009 | Pedro et al. |
| 2009/0070103 A1 | 3/2009 | Beggelman et al. |
| 2009/0112882 A1 | 4/2009 | Maresh et al. |
| 2009/0136102 A1 | 5/2009 | Kimpe et al. |
| 2009/0271221 A1 | 10/2009 | Aridi et al. |
| 2010/0145723 A1 | 6/2010 | Hudson et al. |
| 2010/0179827 A1 | 7/2010 | McCallie, Jr. et al. |
| 2010/0185496 A1 | 7/2010 | Hahn et al. |
| 2011/0077972 A1* | 3/2011 | Breitenstein ........... G06Q 10/10 705/3 |
| 2011/0093334 A1 | 4/2011 | Wood |
| 2011/0225001 A1 | 9/2011 | Shen |
| 2012/0089412 A1 | 4/2012 | Bardy et al. |

OTHER PUBLICATIONS

Korean Intellectual Property Office, ISA, "International Search Report and Written Opinion" in PCT Application No. PCT/US2012/053182, dated Mar. 18, 2013, 12 pages.

The Statistics Calculator, StatPac; Dec. 17, 2003, available from: http://web.archive.org/web/20031217141819/http://statpac.com/statistics-calculator/percents.htm.

* cited by examiner

Example – Referral Inferred by the Model but Not Reported in workflow system

Evidence of Colonoscopy Referral

Patient is being referred by PCP for a colo in regards to BRBPR. Is colo ok to schedule and how soon? XXX, GI Surgery Scheduler --Telephone Encounter. 3/23/12

Evidence of the Colonoscopy Performed

COLONOSCOPY REPORT Endoscopist: XXX, MD
Location: Surgecenter of Palo Alto.   Referring physician: XXX, MD -- Ambulatory Surgery Center. Progress Note.  5/1/12

Fig. 13A

Example - Referral Inferred by the Model but Not Reported

Evidence for Procedure Referral

Can i schedule this patient for an injection at sutter or in-office procedure? ---- Message ----
From: XXX. Sent: 5/10/2012 5:02 PM To: XXX, MD -- Telephone Encounter, 5/10/12

Evidence for Referred Procedure

-- Informed Consent Note for spinal injection, 5/11/12

Fig. 13B

Example – Epic Referral Reporting Incompletely Represents Referral Activity

- Encounter Note from Referring Physician, XXX, MD. Date: 4/26/12.

YYY is a lovely 73 year old female with memory difficulties who returns for follow up.

...
  Plans.
  1) Further work-ups:  a) MRI brain w/o gad ASAP to evaluate the right hemiplegia
  ...
  4) PT for the gait training and OT for the right upper extremity monoplegia

- Epic Referral data for this patient: 4/26/12 to 5/31/12

Referral for MRI, Brain. Internal location.
  Date of Referral: 4/26/12. XXX, MD. Referring physician

Fig. 13C

Example - Referral Reporting Incompletely Represents Consulting Activity

Pain Mgmt Clinic Consult Note. Date: 5/29/12

REF PHYS: XXX., MD
CHIEF COMPLAINT: chronic low back pain and left leg pain....
PLAN: .... I offered the patient to perform a series of lumbar epidurals.

Epic Referral data for this patient

Referral for Pain Mgmt Clinic. Internal location.
Date of Referral: 5/1/12. XXX, MD. Referring physician

Fig. 13D

SYSTEMS AND METHODS FOR MEDICAL REFERRAL ANALYTICS

CROSS REFERENCE TO RELATED APPLICATIONS

This continuation-in-part application claims the benefit of U.S. application Ser. No. 13/798,031, filed Mar. 12, 2013, entitled "Systems and Methods for Patient Retention in Network Through Referral Analytics", which application in a non-provisional of U.S. provisional application No. 61/754,527 filed on Jan. 18, 2013, of the same title, both applications are incorporated herein in their entirety by this reference.

This application is also a continuation-in-part application which claims the benefit of application Ser. No. 13/223,228 filed on Aug. 31, 2011, entitled "Medical Information Navigation Engine (MINE) System", which application claims priority to U.S. Provisional Application No. 61/379,228 filed on Sep. 1, 2010, of the same title, both applications are incorporated herein in their entirety by this reference.

BACKGROUND

The present invention relates generally to a medical information engine, and particularly to management and consolidation of medical information which enables analysis of patient referrals in a medical network for the purpose of optimizing referral practices.

Despite rapid growth of innovation in other fields in recent decades, the world of medical information, including patient medical records, billing, referrals, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One of the challenges facing those in the medical or related areas is the number of sources of information, the great amount of information from each source, and consolidation of such information in a manner that renders it meaningful and useful to those in the field in addition to patients. Obviously, this has contributed to increased medical costs and is perhaps largely attributed to the field suffering from an organized solution to better aid the medical professionals, to better aid those requiring more reliable patient history and those requiring more control and access over such information.

Currently, when a patient sees various medical professionals over the years, there is no method for universally tracking recommendations, thoughts, prescriptions, referrals, or diagnosis. This hinders the job of insurance companies in making certain requisite determinations, physicians making decisions that directly impact the health of the patient, and hospitals and other medical institutions that similarly rely but do not have the benefit of the requisite information, not to mention the patient.

For consolidated provider networks it may be possible to centralize a patient's records. However, these records are typically not available outside of the network, and moreover, often the records generated outside of network are often isolated. Patient referrals, thus can cause increased costs for an insurer, and may result in fragmented patient information. By being able to properly analyze patient referral practices, insurers and health managers would be more able to provide better referral service to patients, increase patient retention, and increase operational efficiency.

It is therefore apparent that an urgent need exists for a health information management system usable to those in the medical field, including patients. A functionality of such a system would be the ability to track patient referrals, and generate models which assist insurers and care providers to track referral practices. Such a system should also be capable of reconciling and intent-based clustering of patient data by applying at least one clustering rule to the reconciled medication information, and presenting the clustered reconciled medical information to a user.

SUMMARY

To achieve the foregoing and in accordance with the present invention, systems and methods for managing medical information are provided. In particular, systems and methods for referral analysis using intent-based clustering of medical information is provided.

In one embodiment, a health information management system is provided which includes the ability to identify explicit referral activity reported into a referral workflow system, infer referral activity not reported into the referral workflow system utilizing intent-based clustering of medical information, and generate reporting metrics from the inferred and explicit referral activity.

The intent-based clustering of medical information receives medical information from a plurality of medical sources. The medical information is reconciled and clustered. Reconciling applies similarity rules to the medical information. Clustering includes applying at least one clustering rule to the reconciled medication information.

Additionally, a referral suggestion may be generated for a specific application. Physicians are selected within a geographic area who are properly specialized for, and/or have a history of managing, the condition, activity, procedure, or diagnosis. This group is then filtered and ranked based upon patient and referring provider preferences and default preferences in order to generate optimized recommendations for physicians to referral to. Referring provider and default preferences may include any or all of the following parameters: past referrals history, aggregated web-content scores, cost efficacy compared to nearest competitors and industry, organizational strategic preferences, etc.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIGS. 13A to 13E show examples of referral evidence useful by the system for analysis, in accordance with an embodiment;

DETAILED DESCRIPTION

Figure 1:
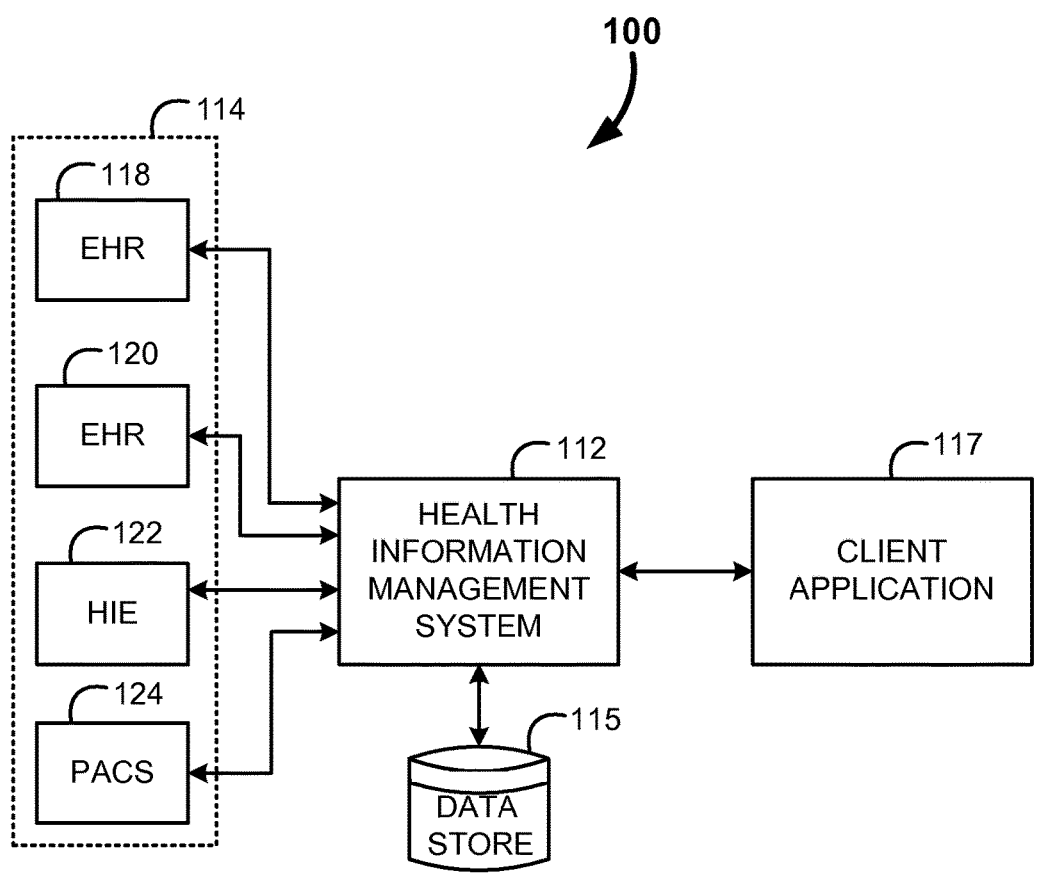
FIG. 1 shows a medical system, in accordance with an embodiment.

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

Referring substantial patient care outside of a Medical Network when equal or superior care is available within the network is not uncommon. These referrals are often uncoordinated and not uniformly reported using existing tracking systems. For most medical providers, it is not clear where these patients are referred or for what reason(s), or what the related costs are. To ensure affordable, quality care and positive patient experience better referral analytics are desired.

Optimization of patient retention in network relies upon three core areas: 1) patient retention enhancement, 2) patient retention management, and 3) enablers of patient retention. The first category of retention optimization relies upon medical network procedures and education in order to increase patient retention. This is well known, but in order to effectively implement these actions, retention analytics, including referral analytics, are desirable. For example, a procedure for placing quality standards for referrals outside of network may not be effective if the practice area rarely engages in referral practices. In a similar manner, patient retention enablers, such as marketing, central logic systems, and set payment rates enable the retention of patients through affordability and quality of care.

As previously noted, in order to drive enablers to enhance patient retention, patient retention management systems are employed. These systems collect data, generate referral analytics, and otherwise compile and analyze relevant data. The health information management system 112 is a particularly powerful tool capable of performing many of these activities.

Referring now to FIG. 1, a medical system 100 is shown, in accordance with some embodiments. The system 100 is shown to include medical information sources 114, a health information management system 112, and medical information consumers/client applications (also referred to herein as "output" or "medical output") 117. The medical sources 114 are shown to include but not limited to an electronic health record (EHR) 118, EHR 120, health information exchange (HIE) 122, and a picture archiving and communication system (PACS) 124.

"Medical information", as used herein, may refer to any health-related information, including but not limited to patient medical records, patient entered information, care team entered information, healthcare device generated information, and billing information.

The sources 114 generally provides various medical information to the health information management system 112. For example, the EHRs 118 and 120 each may provide information such as medical records and billing, the HIE 122 may provide information such as medical records, and the PACS 124 may provide information such as diagnostic imaging and reports.

The medical information consumers/client applications 117, which may be made of a host of entities or individuals, such as patients, clinics, medical institutions, health organization, and any other medical-related party, use information that is provided by the health information management system 112. For example, user-customized processed medical information is provided by the health information management system 112 to a number of client applications 117. In this case, the health information management system 112 generates user-customized processed medical information to a plurality of users, with at least a portion of the user-customize processed medical information being provided to each of the users based on the relevancy of the portion being provided of each user's specific function or role and each user's associated security privileges.

In some embodiments, the health information management system may merely be a repository of health records and information. In alternate embodiments, the health information management system 112 may have sophisticated capabilities which enable it to index, map, and consolidate medical information, received from the sources 114, and also potentially enabling the tagging of this information, and reconciliation of the tagged information. In some methods and embodiments, information that is extracted from images is tagged to enhance recall of search queries. Indexing, at least in part, processes document and converts them into formats that allows for quick searching across a large collection of documents.

In some embodiments, the information in the health information management system 112 is encrypted and secure to ensure privacy of sensitive medical information.

It is understood that the sources 114 of FIG. 1 includes merely some examples of the sources that communicate with the health information management system 112 and that other sources, known to those in the field, are contemplated. Similarly, the output 117 may be used by those or entities not discussed herein but that are contemplated and within the scope and spirit of the invention.

Figure 2:
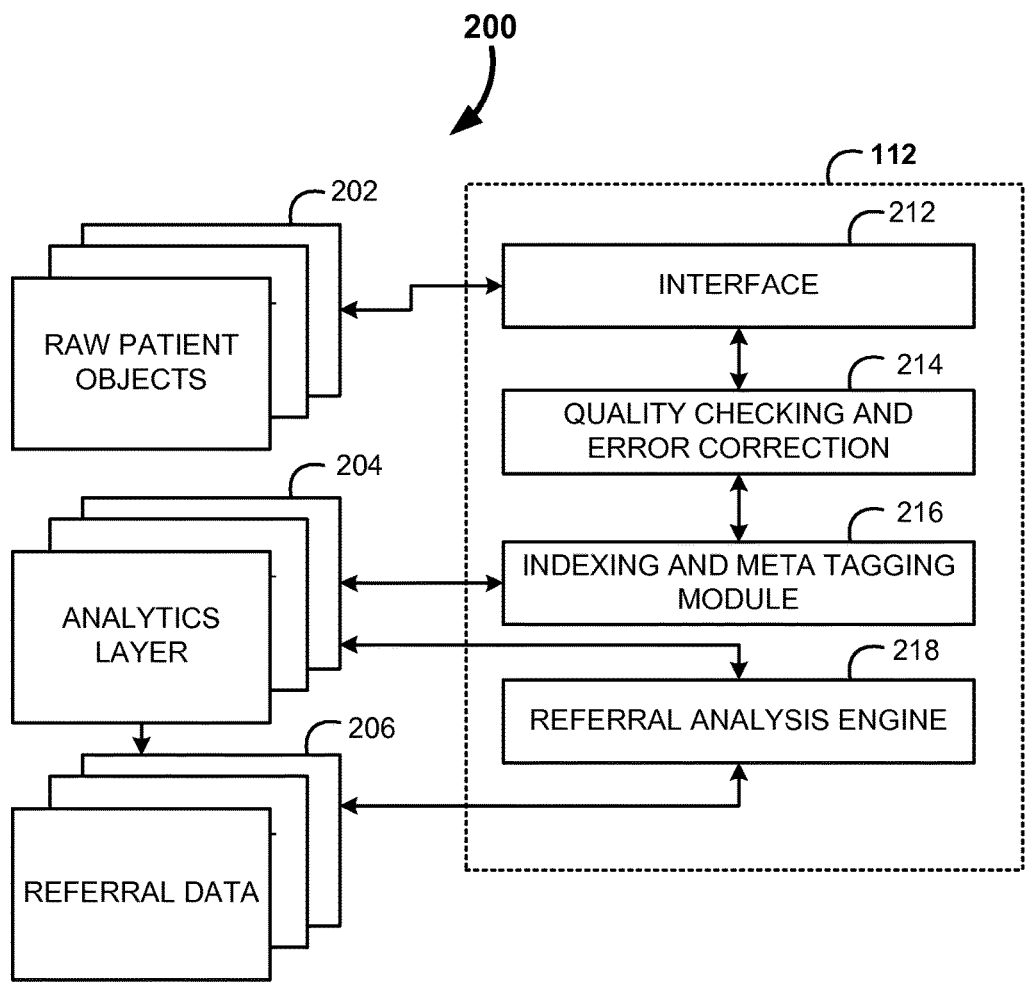
FIG. 2 shows further details of the system within a data architecture, including a referral analyzer, in accordance with an embodiment.

Turning to FIG. 2, a more detailed illustration for the health information management system 112 is provided. In this example diagram, the health information management system 112 is interacting with multiple levels of data storage, shown generally at 200. The storage level begins with raw patient objects 202 which are received from the plurality of sources 114.

The health information management system 112 includes an interface 212 which can collect these objects. These objects 202 may be collected in various forms, such as but not limited to text, html, CCD, CCR, HL7, image and any other type or format information. The interface 212 then provides to the information to a quality checking and error corrector 214, in some embodiments.

The quality checking and error corrector 214 may simply delete duplicate errors and redundant patient medical records, such as, multiple records for the same individual appearing as though the records are for different individuals or multiple data elements that are recorded similarly but slightly differently in the different sources. The quality checking and error corrector 214 may also perform other basic and known error correction processes. Alternatively, more advanced quality checking and error corrector 214 systems may check the quality of medical information provided by various sources 114 by the patients, structured data, and unstructured data, in a Wiki-like mannered setting whereby the users can help maintain and improve the quality of information displayed.

In some embodiments, an indexing and Meta tagging module 216 may utilize a processor to processing the data, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others. The processed data may then be provided to the second level of the data storage architecture, the analytics layer 204. In some embodiments, the analytics layer 204 may be transient.

Analytics modules may take information from the analytics layer 204 and perform certain tasks on the information, which may include query, search, presentation, and quality checking. One such analytic is the referral analysis engine 218 which parses through the data of the analytics layer 204 to identify referral activity for a patient. This referral data 206 may be utilized for further analytics such as patient retention, patient follow-up analysis, and referral suggestion generation.

Figure 3:
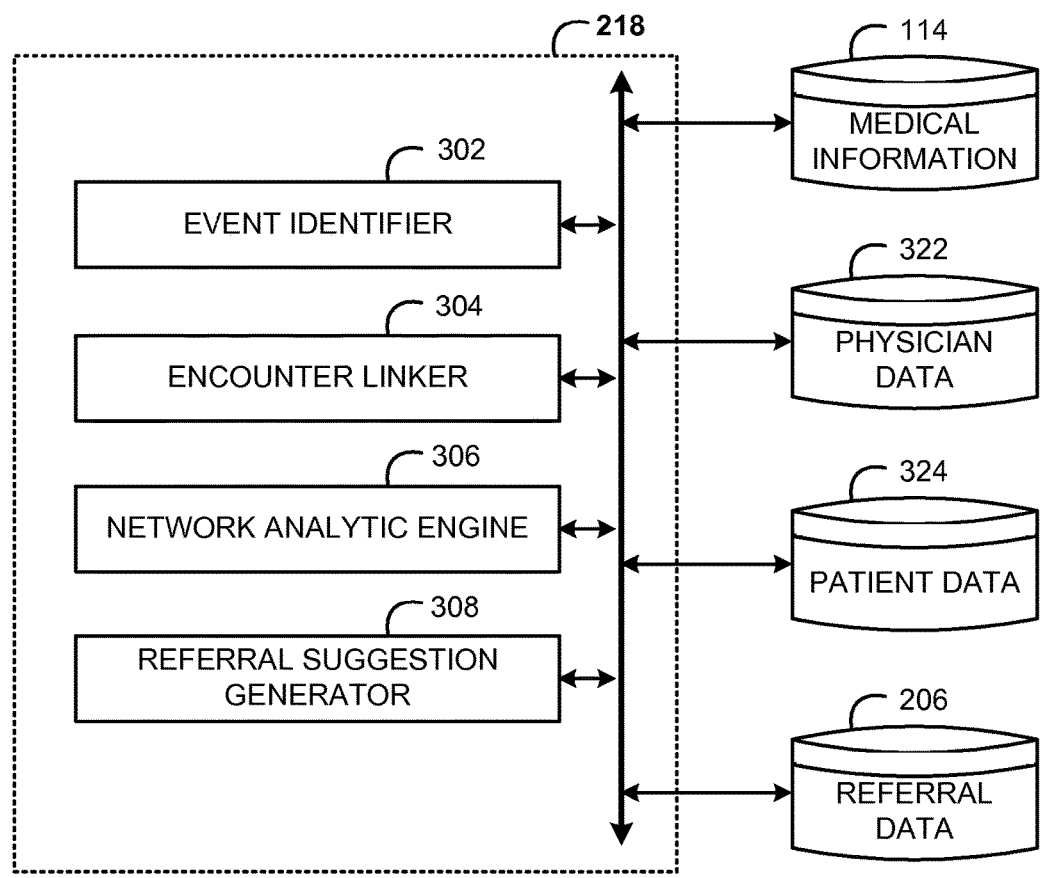
FIG. 3 shows an exemplary embodiment of the referral analyzer, in accordance with an embodiment.

Turning to FIG. 3, a more detailed illustration of the referral analysis engine 218 is provided. Here it can be seen that the referral analysis engine 218 includes an event identifier 302, an encounter linker 304, a network analytic engine 306, and a referral suggestion generator 308. These subsystems may be logically of physically coupled within the referral analysis engine 218. The referral analysis engine 218 may also include, or have access to, databases of medical information 114, physician data 322, patient data 324 and the referral data 206.

The event identifier 302 utilizes the medical information 114 to infer encounter events that result in referrals. Referrals may sometimes be explicitly documented. In these cases, identifying a referral event is relatively trivial. However, in many situations, referrals events are not explicitly identified. Rather these referral events must be inferred from other evidence. The inference of a referral event is described in greater detail in reference to following figures.

Even after a referral is identified, the system must determine if the referral was ever followed up upon by the patient, and if so, which subsequent encounter resulted from the referral. The encounter linker 304 performs this analysis by looking at what kind of follow-up action would result from the referral encounter, and identifying any such event in the appropriate timeframe. For example, if a patient is diagnosed with an irregular heartbeat, and within a month undergoes a stress test, the system may infer that the stress test was the resulting referral activity for the initial finding.

The network analytics engine 306 compiles the referral activity as it pertains to insurance networks. Cost and quality of care are more readily controlled when care is undergone within established health networks. The network analytics engine 306 determines the financial and quality of care impact that a referral activity has dependent upon if the referral follow-up is performed in or out of network.

Figure 4:
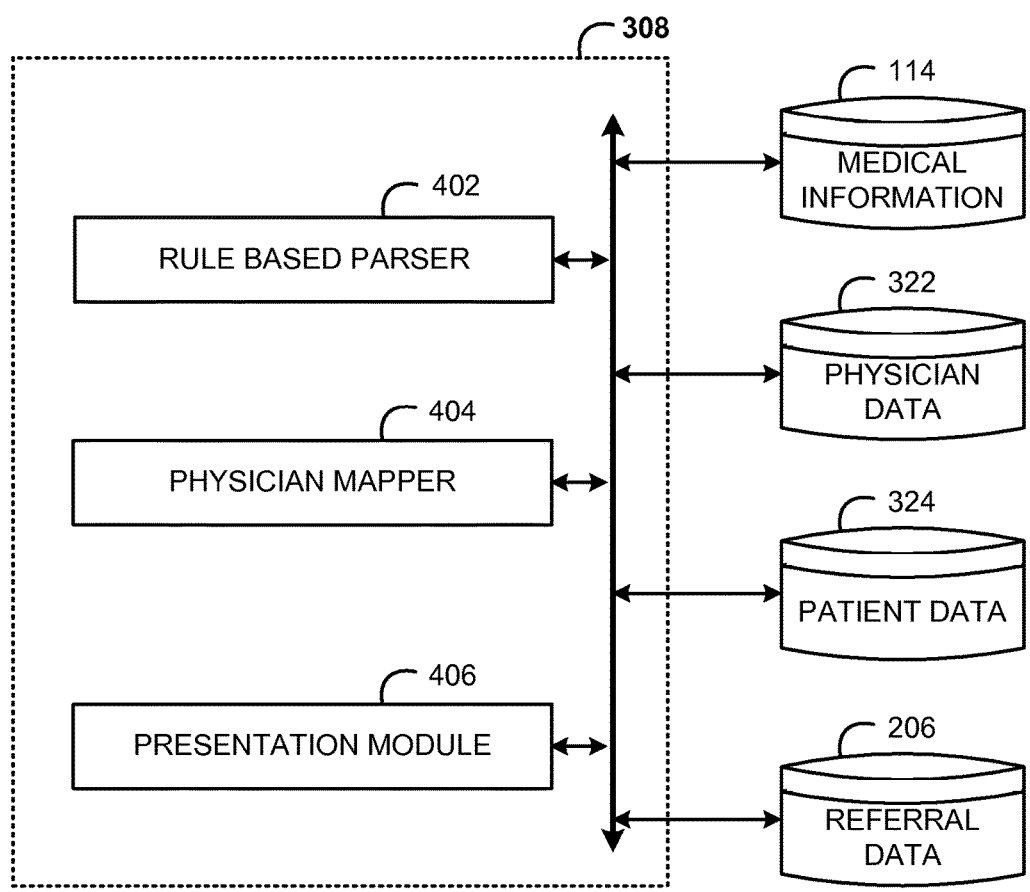
FIG. 4 shows an exemplary embodiment of the referral suggestion generator, in accordance with an embodiment.

The referral suggestion generator 308 is provided in greater detail in relation to FIG. 4. The referral suggestion generator 308 may be employed to generate suggestions for referral activity to a doctor or patient that optimizes patient care, convenience, and financial burden. The referral suggestion generator 308 could be employed on-the-fly to provide patients immediate referral suggestions. Alternatively, the referral suggestion generator 308 could be a web-based tool, accessible by patients to assist in physician selection. Lastly, the referral suggestion generator 308 could also be utilized in the background in order to analyze for optimal referral patters to assist in physician training, policy generation, and as a performance measure.

The referral suggestion generator 308 includes a rule based parser 402, a physician mapper 404, and a presentation module. The referral suggestion generator 308 takes in referral data 206 and medical information 114 to identify when the referral suggestion is required, and further the kind of referral activity required. Patient data 324 may likewise be queried to identify patient preferences, habits and the like. An important factor in referral activity is patient convenience. If a patient does not find follow-up activity sufficiently convenient, their likelihood of adhering to the follow-up diminishes. Non action for a referral is often wasteful, and results in poorer medical outcomes.

Patient data may include information such as average distance a patient is willing to travel to see a specialist, and patient specific data such as doctor preferences (i.e., gender, language spoken, medical school, age/years in practice, established doctor relationships, etc.) personal location/distance constraints, likelihood of adhering to follow-up procedures, etc.

These preferences and referral events may be reduced to constraints that are provided into the rule based parser 402 which then parses out the appropriate physicians. For example, if the referral activity is surgical ontological treatment, the rules may require that the referral is for physicians which have specialization in that type of oncology, within a large geographic area. In contrast, if the referral is for a prenatal follow-up, any obstetrician gynecologist may be referred, but the rules may be more restrictive as to the patient's gender preferences, location preferences, existing relationships, etc.

The physician mapper 404 next provides, from the listing of eligible physicians, a sorting of those physicians. This sorting of physicians may include an optimization for a variety of objectives including patient outcome, overall cost, patient preferences (convenience), past referrals history, aggregated web-content scores, cost efficacy compared to nearest competitors and industry, organizational strategic preferences, etc. The data may then be sent to the presentation module 406 for display to the user. Presentation may be as simple as providing a short listing of names with contact information. Alternatively, the presentation may include additional metrics to the user, such as physician reviews (where available), distance from the referral to the patients home or office, financial impact of the referral (both in total, and upon the patient), and any other data which may be desirable for referral selection.

For avoidance of doubt, the foregoing modules and engines may be software programs, executed by a computer or computing engine of suitable sorts, or may be implemented in hardware, or a combination thereof.

Figure 5:
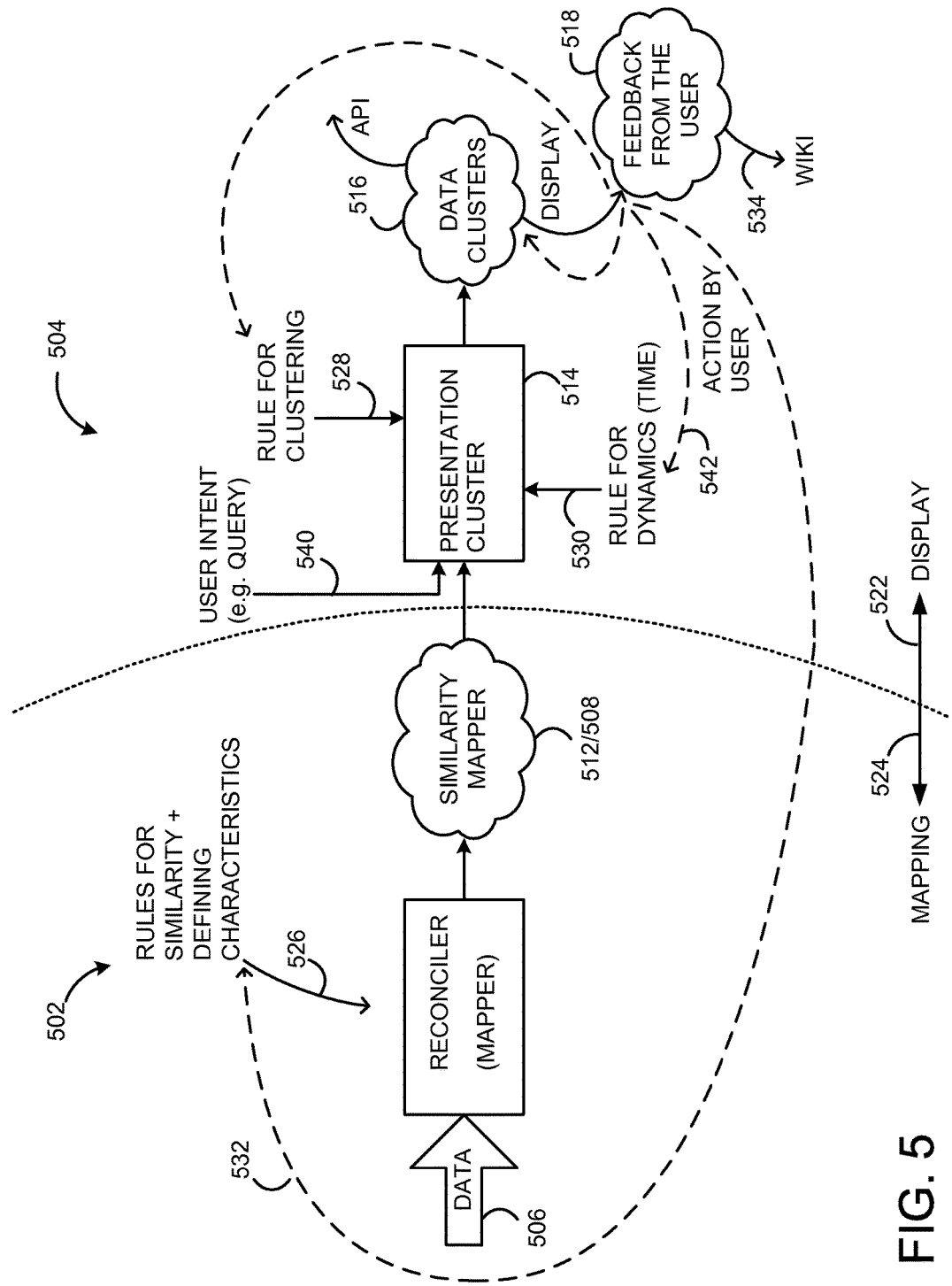
FIG. 5 shows an exemplary embodiment of a logical diagram for clustering analysis which may be employed for referral analysis, in accordance with an embodiment.

FIG. 5 shows some of the analytical components which drive the ability to identify referral events and link them to follow-up procedures. FIG. 5 includes a reconciliation engine (also referred to hereinafter as the "mapper") 502 responsive to data 506, which is, at least in part, within the source 114, and is shown to provide reconciled information that is provided to the intent-based presentation block 504.

The engine 502 advantageously learns, through history, ontology, user-input, the type of user, and a host of other factors, similarities between various information from the data 506, defines characteristics thereof, models this information conceptually, pre-selects and sorts information before providing it the block 504 for presentation in the form of a display, or other known types of presentations. Such processing entails the use of various sets of rules, at various stages, as will be evident shortly relative to subsequent figures and discussions.

Presentation by the block 504 is intent-based, that is, the user, along with history, and other factors are used to determine the information to be presented. With time, as the engine 502's knowledge of medical information, such as drugs, type of users, diagnosis, the relationship between various diagnosis/diseases relative to each other and relative to various medications, and other information, increases, the information presented by 504 becomes increasingly intent-based.

The engine 502 is shown to include a reconciler block 510 that receives data 506 and a similarity mapper 512. The block 504 is shown to include a presentation cluster block 514, which is shown to receive information from the mapper 512, and a data cluster 516.

A set of similarity rules 526, which identify similarities of various types of information, and define characteristics thereof, is shown being utilized by the reconciler 510. The rules 526 are applied to the data 506 to identify similar concepts, which unlike prior art techniques, is not to look for matches and rather to correlate information based on concepts. Through feedback from users 518, this becomes a learned process with improved and more sophisticated conceptual similarity detection. The similarity mapper 512 maps the reconciled information, generated by the reconciler 510.

Another set of rules, namely, a set of clustering rules 528, is provided to the presentation cluster block 514 for determining which information, if any, to cluster or group. The block 514 also receives as input, user intent query 540, from a user, and applies the rules 528 to the latter. The rules 528 are used by the block 514 to group information received from the mapper 512, based on the user intent query 540, and in the process additionally apply a set of dynamics (time) rules 530 thereto. The rules 530 serve to identify what is to be looked at to find what information has been changed over time. In this respect, feedback from the user, through 542, is utilized. Similarly, the rules 528 utilize feedback from the user. Additionally, feedback from the user is utilized, at 534, to accumulate concept-based information and definitions in a Wiki-style fashion.

The presentation cluster block 514 generates output data clusters 516. The cluster 516 information may be displayed and/or presented in other manners, such as with an Application Programming Interface (API), and it further may receive user feedback and use the same to further refine rules for clustering and similarity mappings.

The rules 526, 528, and 530 are independent of one another in some embodiments of the invention. In other embodiments, information flows there between. Advantageously, these rules, partly because they are applied at different stages in the processing of the data 506, allow for a learned and conceptualized process as opposed to a hard decision. For example, in current techniques, where only one set of rules are utilized early on in the processing of the data, a hard decision is made with no flexibility to alter this decision thereby increasing the risk of mis-categorization and/or identification of relevant information. In contrast, thereto, the different sets of rules of the embodiment of FIG. 5, breakdown categories, such as similarity, display, and history, allows configuration of various aspects thereof.

By way of example, in prior art techniques, where the data is regarding electronic devices and a cell phone is to be identified, where the single set of rules, made early on in the process, is based on the lack of a keyboard, and a central processing unit, the device may be erroneously identified as an electronic tablet, with no recourse. Whereas, the embodiment of FIG. 5 allows for progressive learning of various attributes of the device by, for example, using the above exemplary rules as the rules 526 but based on the rules 530 and 528, introducing attributes, such as size of the device, that allow for a more accurate identification of the device. And further, due to the user-feedback and query, allow for dynamically altering the rules.

Use of various rules, such as rules 526, 528, and 530, at various stages of processing, allows flexibility in applying the rules to achieve greater accuracy of clustering. In medical applications in particular, information is oftentimes duplicated for various reasons, such as lack of standardization of names of medications, shorthand identification of information, and a slew of other reasons. In this regard, flexibility of applying rules is vital. While three sets of rules are shown in the figures and discussed herein relative to various embodiments, it is understood that a different number of rules may be employed.

For a better understanding of the flexibility the system described above offers, an example is now presented. Suppose the data 506 carries medical information for which a particular condition, e.g. diabetes, is to be detected. Rule 526 allows for a similarity between lab results and "diabetes" to be identified but that is nearly where the application of rule 526 ends until further information is known and extracted later in the processing of the data 506. Namely, when rule 528 is applied to the outcome identified by Rule 526, the lab results are crawled or inspected for "diabetes" or another identifier for "diabetes". Additionally, the presence of various relevant labs is detected and the association between the presence of the labs and the problem of diabetes and perhaps, hemoglobin A1c (a measure of average blood glucose concentration over the past 30 to 120 days, used in the diagnosis and treatment of diabetes) is made. Next, the rule 530 is applied to the outcome of the application of rule 528 where patient data is used or a correlation between a problem and a treatment for a large percent of the patient population is made. Specifically, the percentage of patients with diabetes is detected. The parameter of time allows for the latter detection, otherwise, for example, at the application of rule 526 or even rule 528, a large patient base could not have been correlated.

The user input at 540 and the user feedback at 518 all help in the clustering of data. At the application of rule 526, a determination is made as to how things are similar until a user asks about the similarity after which a more educated application of rules is performed. Thus, no decision is made until the end or at the output of the block 514, in real-time.

During the application of rule 526, the system is informed of key parameters but not how to put the data together. Then, during the application of the rule 528, the system is informed of how to put the data together (cluster) by aligning the data in a particular manner. Application of rule 530 determines how things change over time, or not, but not what the correlation or similarity actually is, which is generally done through the rule 528. Part of the reason for splitting the rules is to delay decision-making as long as possible in an effort to cleverly use more information, such as that provided by the user, for an increasingly accurate finding.

The outcome of the data cluster 516 can be transmitted to another processor, system, user, or any other entity.

Another example of the manner rules are employed, outside of the medical community, is for example, in determining parameters of hair where rule 526 is used to look for length of hair and rule 528 uses the outcome of the length of hair to further determine alopecia as compared with normal hair growth. Rule 530 may then be used to determine a percentage of a demographic that has experienced baldness. Further examples of the application of these rules is shown and discussed relative to FIGS. 6-11.

It is understood that the blocks shown in FIG. 5, such as block 510 and 514, and 516 may be independently a machine and/or processor or a part of a machine and/or processor. They may alternatively, be carried out in software programs.

Figure 6:
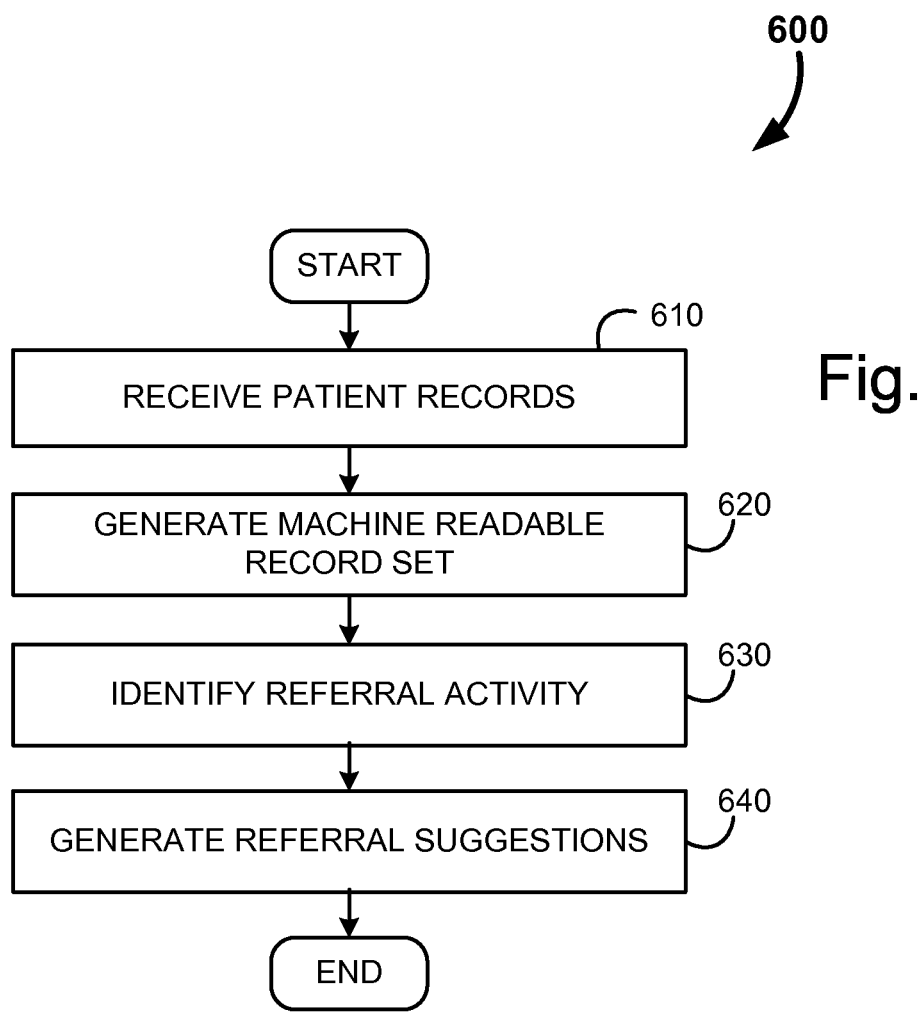
FIGS. 6-9 show flow charts for the process of referral analysis, in accordance with an embodiment of the invention.
Figure 10:
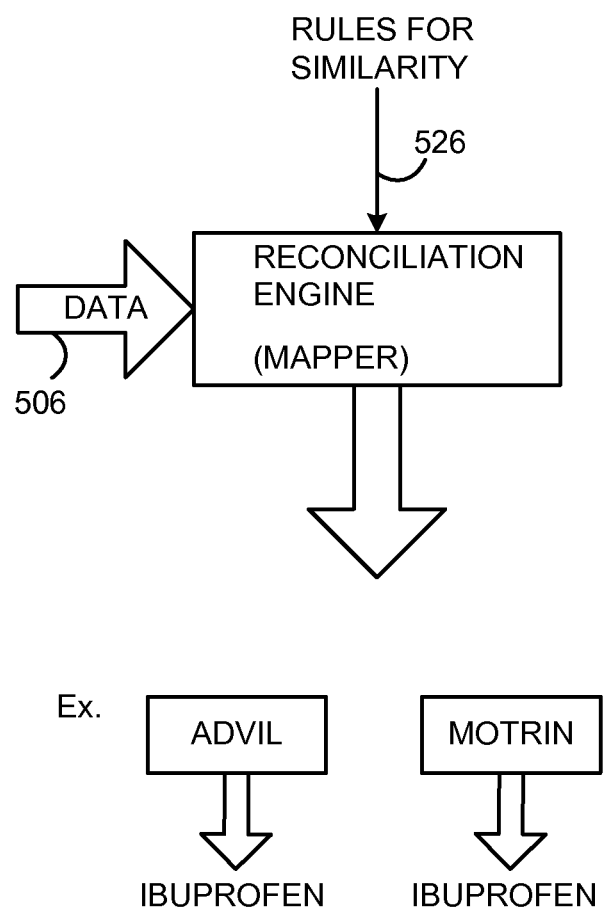
FIGS. 10 and 11 show example illustrations of a mapper reconciling varying terms to consistent meanings, in accordance with an embodiment.
Figure 11:
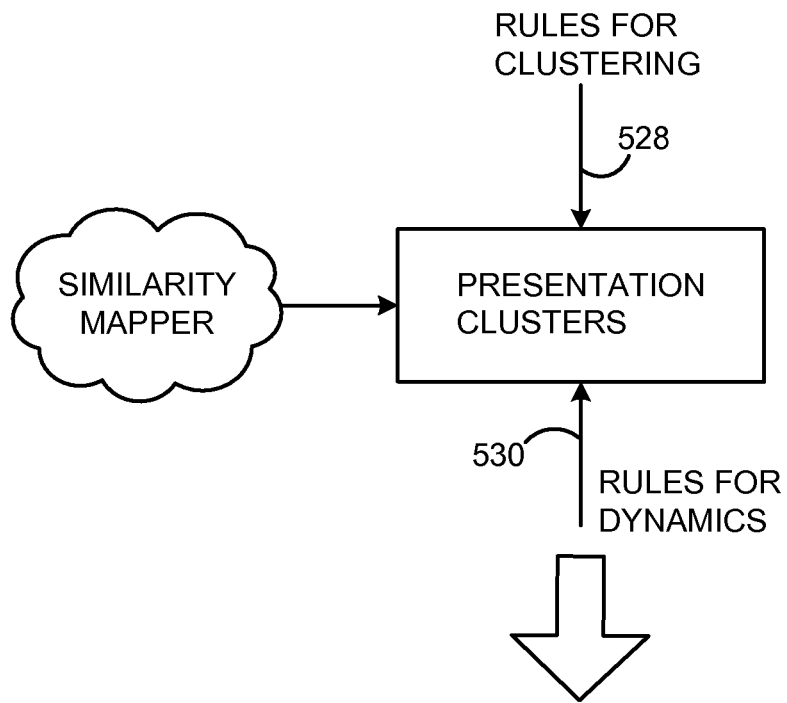

Moving now to FIGS. 10 and 11 each show examples of applying the rules 526, and 528 and 530, to the data 506 to yield certain beneficial results. In FIG. 6, rule 526 is applied to the data 506 to identify the medication named "Advil" as an "Ibuprofen". Similarly, "Motrin" is identified as Ibuprofen, therefore, allowing more flexibility to a patient and a medical professional in deciding to use these drugs. Rules for similarity specific what characteristics need to be looked at to determine similarity of an object to another object.

Using the same example, rules 528 and 530 may be applied to the outcome of the rule 526 to the data 506 to determine other information based on the intent of the user. For example, the dosage of Ibuprofen, from all sources, even those with other ingredients, may be determined by applying rule 528, after applying rule 526 such that the outcome of rule 526 detects Ibuprofen types of medications and rule 528 narrows the detection to those with a threshold dosage.

FIG. 11 shows an application of the rules 528 and 530 where a set of associated terms, m1(c), has been identified and another set of associated items, m2(c), has been identified. For example m1(c) is one medication, m2(c) is another medication and "c" are particular characteristics of each medication such as, but not limited to, brand name, generic name, dosage, prescription instructions (sig), prescription date, and start date. Rules for dynamics, rule 526, is the time base characteristics. Rules for clustering, rules 528, would be probability of matches of other characteristics. For example, for a given medication such as oral contraceptive pills (OCPs), the rules of dosage might be ignored such that different prescriptions with different doses would be considered the same for clustering purposes. In this example, the use of oral contraceptive medications at all dosages is contraindicated for women with a genetic predisposition or other risk factors associated with thrombotic events (e.g., venous thromboembolism). Another medication where dosage might be very important to outcomes would not be clustered together if the dosage were different. For example, Warfarin, a medication commonly used to prevent blood clotting, has a very narrow therapeutic window and its metabolism widely varies among individuals. The dosage of Warfarin is highly correlated to outcomes of interest. Physicians routinely prescribe different dosages of Warfarin to treat or prevent thrombotic events or predisposing conditions such as pulmonary embolism or atrial fibrillation.

For further clarification, in the example of Advil and Ibuprofen, if the intent is to investigate whether the current dosage of Ibuprofen is too high, all sources of ibuprofen (even those with other ingredients) are better to be identified, in which case the set m1(c) may represent all sources. The date may also be an indicator, such as the last day or week this medication was prescribed or consumed and may accordingly be a part of the set, m2(c). In contrast, if contributors to (or indicators of) a chronic condition is the intent, a longer history (months, years) and the chronic condition itself would be "related" despite low "similarity". Thus, through the flexibility of the application of various rules, such as rules 526, 528, and 530, there can be different ways of displaying information, from the data clusters 516, about a concept under different intents.

By way of further explanation, the rules 528 are used to determine what is considered inside the cluster and the rules 530 is how things in the cluster change over time. Though, in other embodiments, other types of rules are anticipated and other numbers of rules are anticipated. Using the Advil/Ibuprofen example above, the rules 528 are used to determine whether other medicines belong in the display cluster, for instance if they contain Ibuprofen but they also contain other things (such as sleep aid, Comtrex) that may or may not "belong" in the display cluster. The embodiment of FIG. 5 advantageously learns whether they "belong" or not. Through the rule 530, the Ibuprofen cluster might emphasize recent events (past week) in the ranking. Other clusters may interact differently with time.

In a similar vein, the disclosed systems and methods are likewise capable of clustering providers by using provider information. Such clustering matches physicians across geographic area, name, similar practice groups, specialty and past referral pattern to disambiguate the providers. Generally, referral inferences do not include a unique identification for the provider, and as such, these clustering techniques are relied upon to accurately identify the referral provider. For example, some names are unique, with only a single provider in the geographic area of the patient. However, in other situations, the provider name may be common enough where past referral activity, network connections (part of related practice groups), specialty cross-referencing, and the like may be relied upon to determine which provider has been referred. In addition, the system may score the available evidence for this disambiguation in order to generate a confidence score for provider disambiguation.

Returning to FIG. 6, a process flow diagram is provided for referral analysis, shown generally at 600. In this example process, the patient medical records are initially received (at 610) in the manner disclosed previously. The medical records are converted into a machine readable record set (at 620) via the rule based systems disclosed above.

Figure 7:
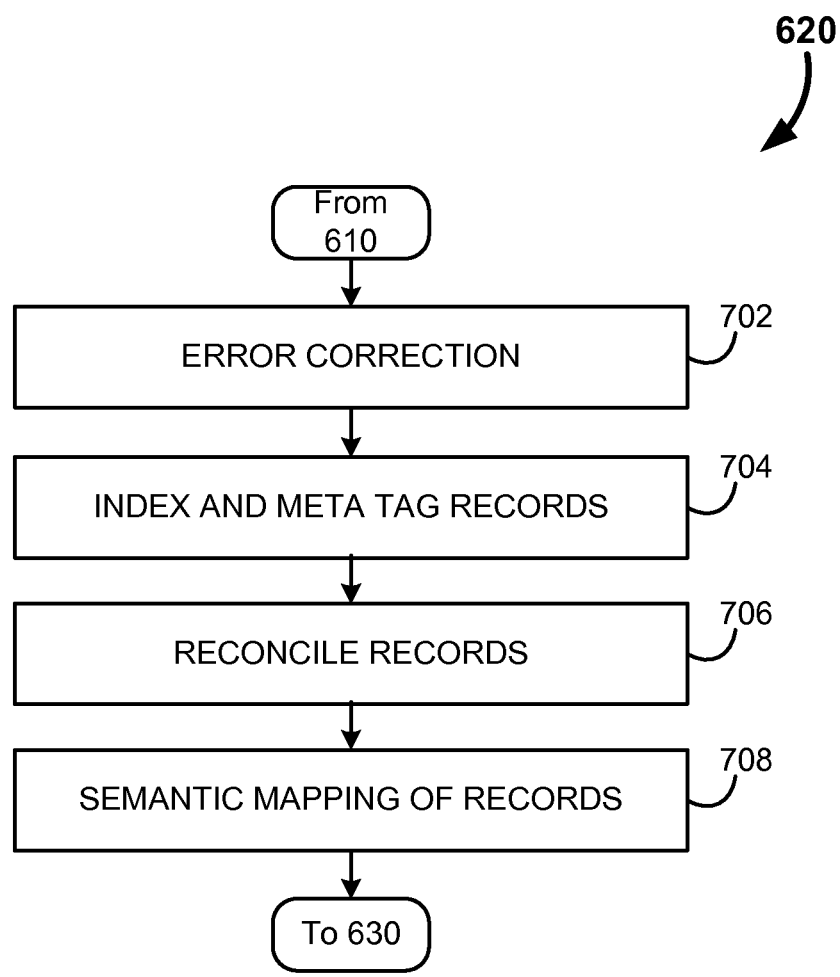

Turning to FIG. 7, a more detailed process flow for the step of converting the medical records into machine readable format is disclosed. Initially an error correction step (at 702) removes duplicate records, incomplete records, and nonsensical records. The corrected records may then be provided for indexing and meta tagging (at 704). Indexing takes processed documents and converts them into formats that make it easy to quickly search across a large collection of documents. Semantic meta-tagging embeds information into the medical information that is relevant thereto and that can be later used to search for certain information for the purpose of reconciliation (at 706) and search, among many others. Next, the records undergo semantic mapping (at 708) as disclosed previously in relation to FIG. 5.

Figure 8:
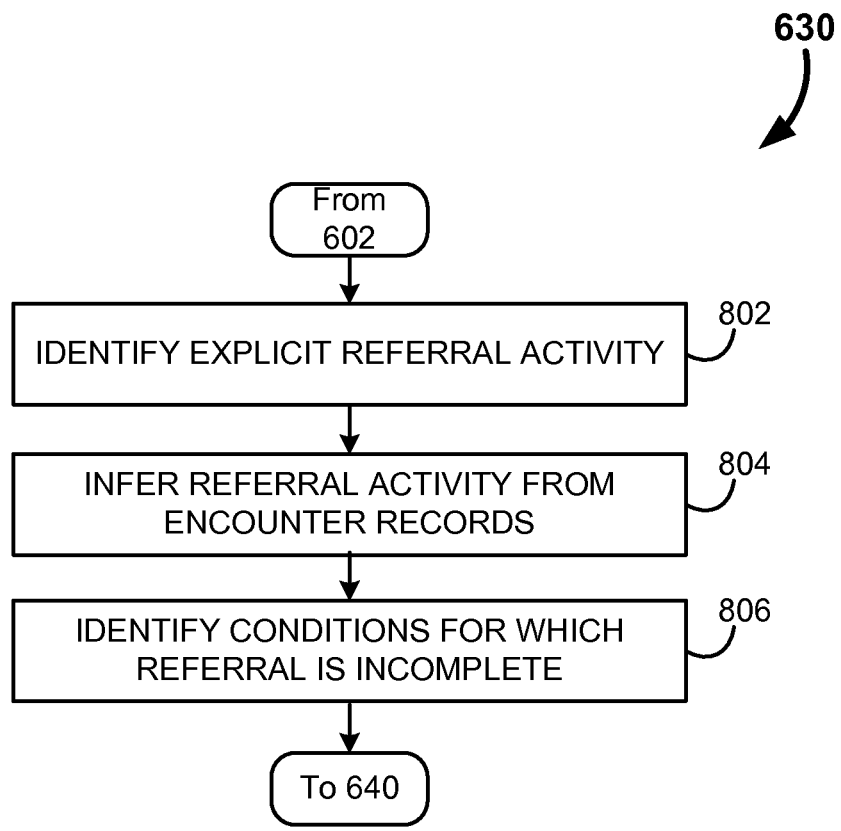

Returning to FIG. 6, after generating machine readable record set, the process continues by identifying referral activity (at 630). FIG. 8 provides a more detailed description of this process, whereby initially explicit referral activity is identified (at 802). Explicit referral activity may include references within the physician records for the patient indicating that the patient was referred for additional tests and/or procedures. However, a large percentage of referral activity is never explicitly recorded in this manner. Therefore, the process must also infer referral activity from the encounter records (at 804). Examples will be provided below which further illustrate how referral activity can be inferred from the medical records. Generally, however, the system identifies where further work-up is requested or necessitated by the patent encounter records. For example, if a patient encounter indicates that the patent sought care for heart palpitations, and the encounter notes indicate an abnormal ECG, however there is no mention of following care, the system rules may infer that such a potentially severe condition would necessitate yet further follow-up care. Thereby inferring a referral event. Further, the process may identify follow-up encounters that are the result of the referral event (at 806). This includes identifying where a referral event exists, and yet no follow-up is evident. By matching subsequent encounter notes and comparing it to the referral activity suggested by the referral event. If they are similar, then the subsequent encounter may be determined as being the resulting referral activity. Likewise, if no such subsequent encounters match the referral activity, then it can be determined the patient has not followed-up on the referral.

Figure 9:
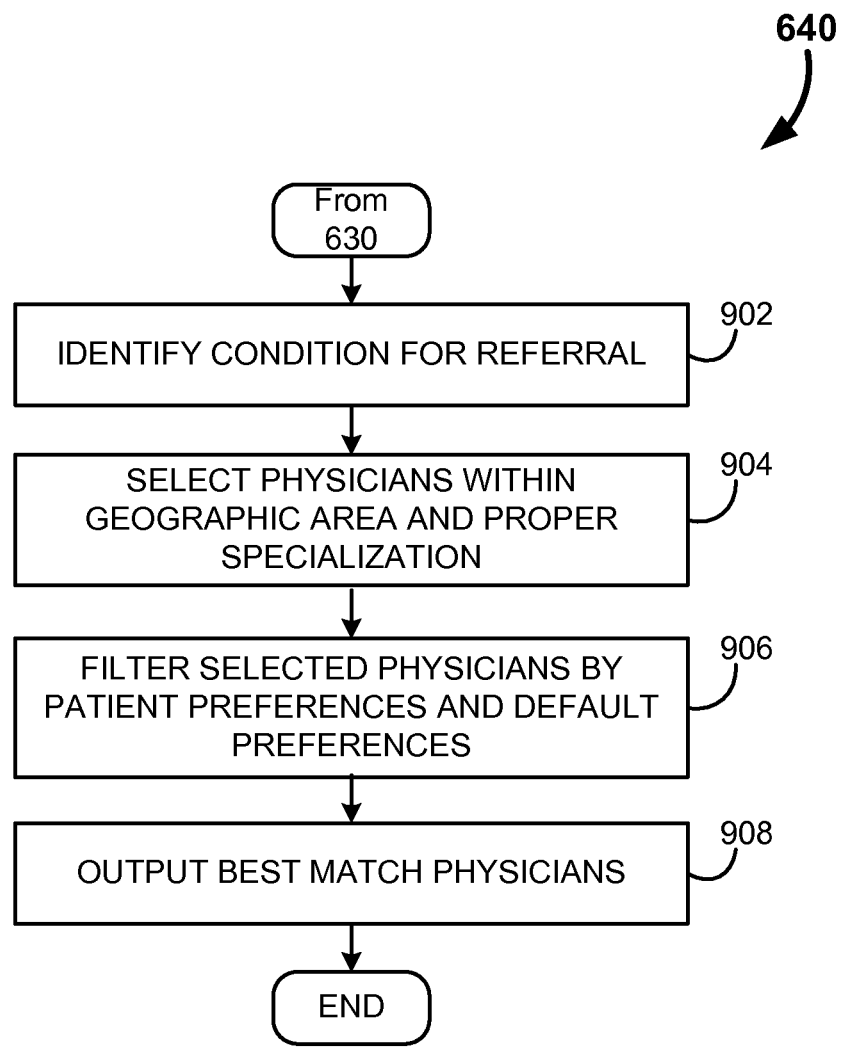

Returning to FIG. 6, once referral activity is identified, in some situations the process may also benefit from generating a referral suggestion (at 640). FIG. 9 provides a more detailed process description of this referral suggestion generation. Note that this process may be tied to the identification of referral activity, as presently indicated, or may be a standalone process.

Referral suggestion initially starts by determining which condition for which the referral is being generated (at 902). Often a physician will provide an exact condition or activity for which the referral is desired; however, in alternate situations the system may be adapted to identify the condition from encounter records using the above disclosed rule based analysis. Physicians or specialists within a set geographic area who are properly specialized in, and/or have a history of managing, the condition, activity, procedure, or diagnosis, that was identified may be selected (at 904). The geographic area is determined by the patient's home and/or work address. A set distance may be prescribed from these locations in order to define the geographic parameter. Patient preferences may further refine the geographic area (i.e., the patient does not mind traveling further than average, the patient is restricted to public transportation, or the patient has particular areas where they would like their care provided, for example). In addition to patient specific alterations to the geographic area, the condition type may impact the area covered by the search. Generally, the more serious or rare the condition, the further patients are willing to travel for a referral. Likewise, less serious conditions typically limit how far out of their way a patient is willing to travel.

Next, the selected physicians are filtered by patient preferences and default preferences (at 906). For example, a patient may desire a physician with a specific gender, or time practicing their specialty. Where care success rate statistics are available, or patient reviews of the physician, these factors may likewise be incorporated into an optimization algorithm in order to output the best matching physician(s) for the referral (at 908). Additional factors used to determine optimal physicians include their hospital admittance privileges, financial cost to the patient and/or insurer, in versus out of network physicians, board certifications, past referrals history, aggregated web-content scores, cost efficacy compared to nearest competitors and industry, organizational strategic preferences, and the like.

Figure 12A:
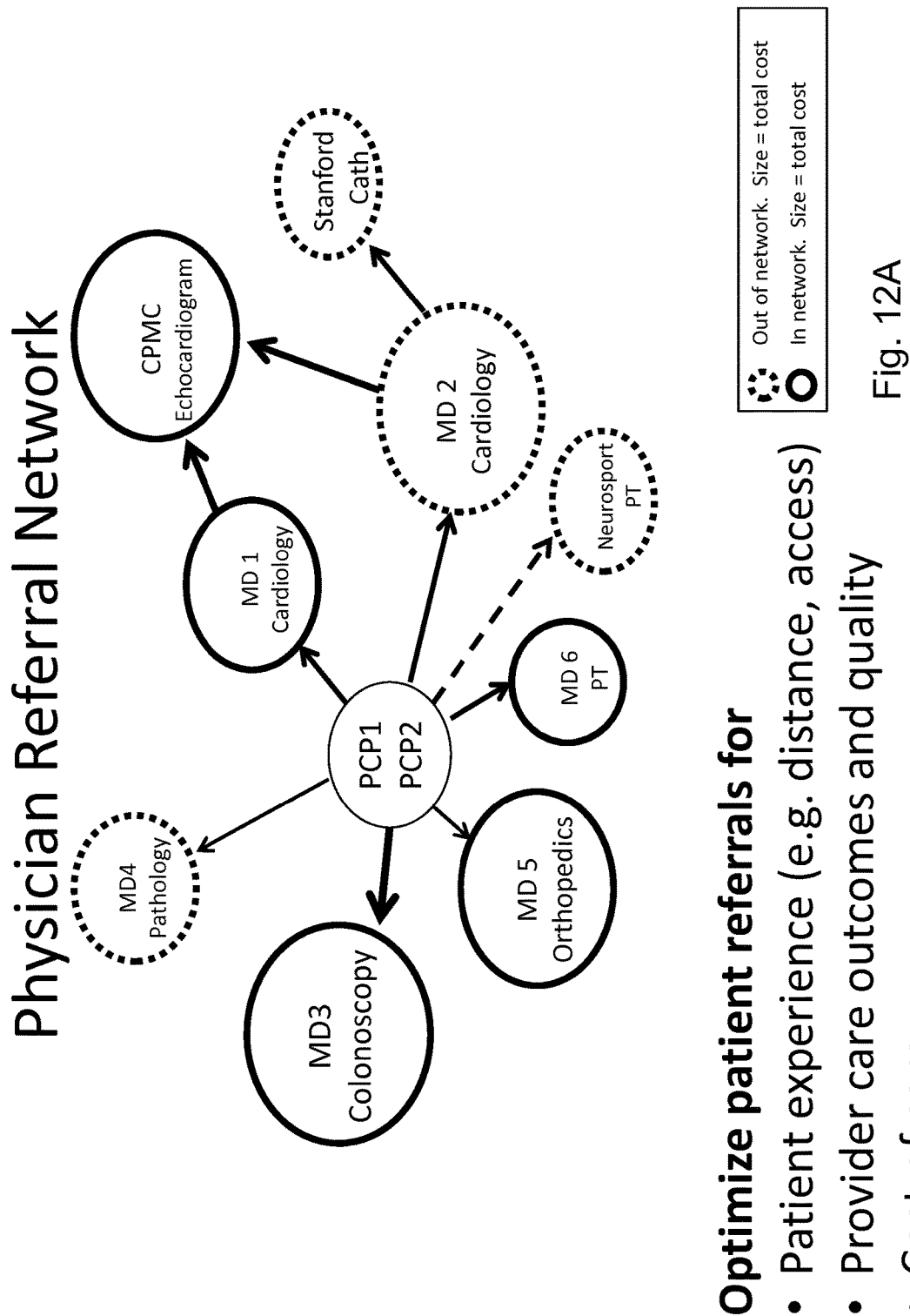
FIGS. 12A and 12B show example logical diagrams of referral networks, in accordance with an embodiment.

Moving to FIG. 12A, a physician referral network is illustrated, for context. The goal of any patient referral optimization is to ensure the best patient experience, outcomes and cost. This illustration provides a representative example of what a typical physician referral network may look like, and relative costs associated with the various providers.

Figure 12B:
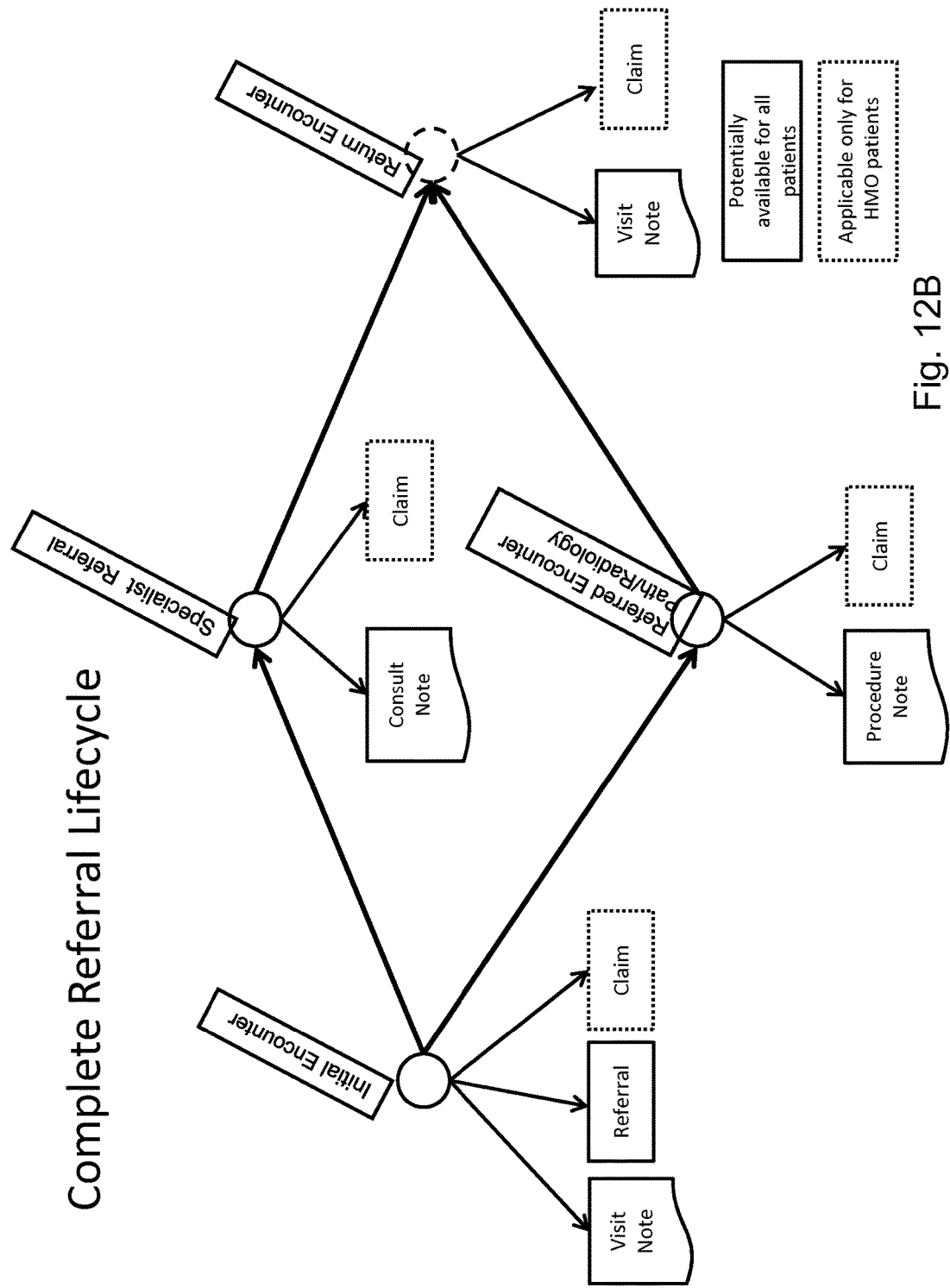

FIG. 12B provides an example diagram for a complete referral lifecycle. In this example, a patient has an initial encounter which yields a visit note, a referral and a claim. The referral may be for a specialist or an internal referred encounter. A procedure note or consult note are generated from this interaction. A return encounter is then made, with the generation of another visit note. These records of the encounter may be utilized by the health information management system 112 to determine referral activity in ways currently not possible without manual review of each note.

The health information management system 112 is able to analyze all referral data to establish an analytical dashboard that provides benchmarking, outcome measures, and enables knowledge driven care. Existing referral workflow systems (i.e. Epic, etc.) only have the ability to report, track and manage referrals if entered. Currently, most referral data is undefined, untrackable and unmanageable, thus making referral workflow systems inefficient. The health information management system 112 is capable of picking out the referral data in a manageable form for consumption by the referral workflow systems. With more robust referral data, these referral workflow systems will be able to assist in the development of strategies that optimize access, continuity of care, resource management, affordability, quality, and patient/physician satisfaction.

The disclosed system may then utilize the referral data to generate one or more metrics of compliance by physicians to preferred referral reporting. An example of such a metric is defined by Formula A:

$$\text{Formula } A = \frac{\text{Number of in network referrals reported in the workflow system}}{\text{Total number of in network referrals}}$$

Further, a second metric can be computed which reveals opportunities for improvement of out of network reporting. An example of such a metric is defined by Formula B:

$$\text{Formula } B = \frac{\text{Number of out of network referrals reported in the workflow system}}{\text{Total number of out of network referrals}}$$

The denominator values for these metrics necessitate the usage of the health information management system 112 to scour patient records in order to capture all incidences where a referral is given.

Lastly, while the architecture of the health information management system 112, and the analytics performed to capture referral data that is otherwise not reported has been disclosed in considerable detail, specific examples of referral modeling are helpful for further clarification. FIGS. 13A-13E provide such examples.

For instance, in FIGS. 13A and 13B, physician notes can be analyzed for a specific procedure referral, even when the referral has not been reported into a referral workflow system. In contrast, FIGS. 13C and 13D provide an instance where referral activity is being reported in the workflow system (MRI referral) but the physician's notes provide a more complete story (referral is also for occupational therapy).

Figure 13E:
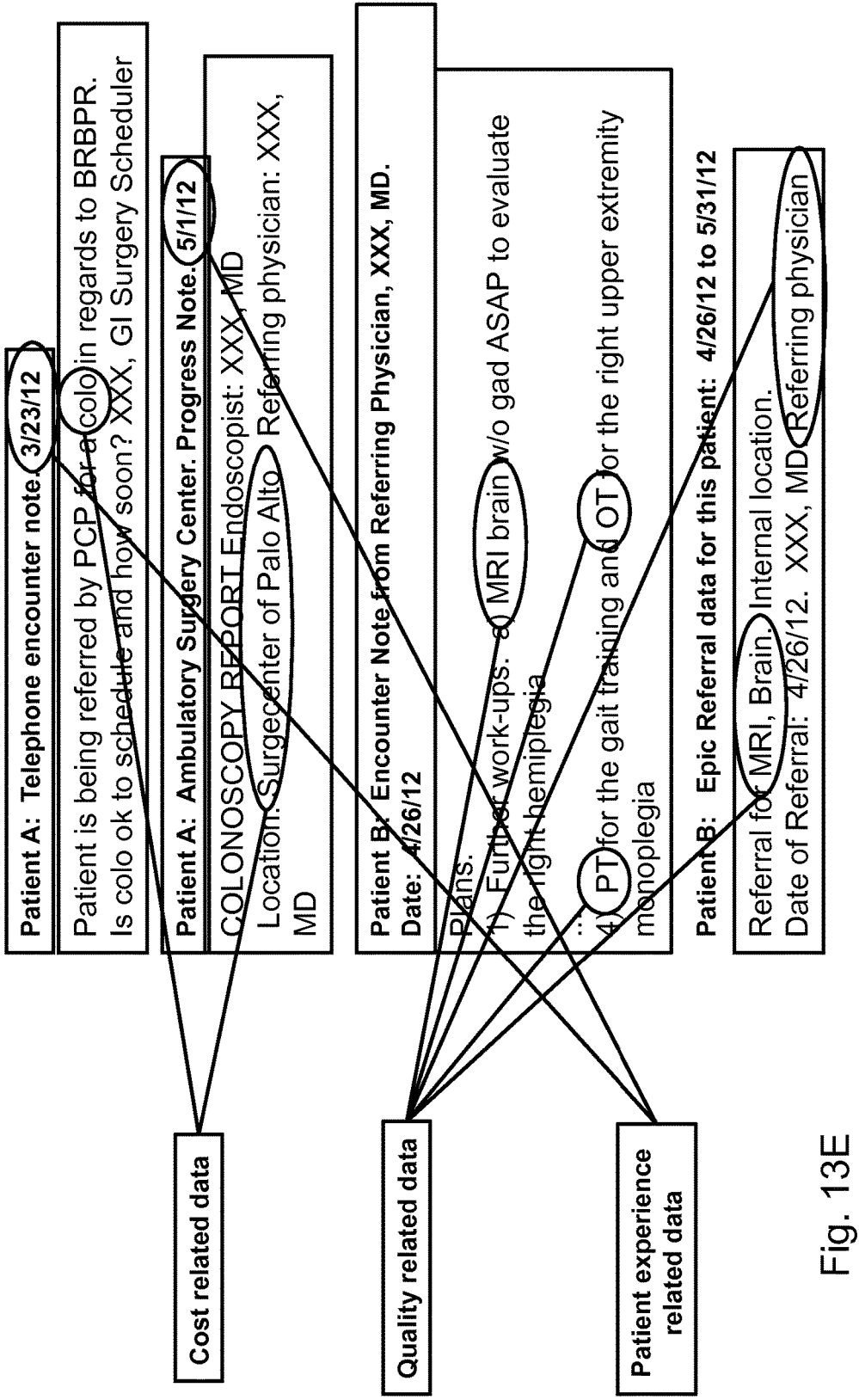

FIG. 13E provides an example of which data is deemed relevant for some embodiment of the health information management system 112 as part of the analysis. This includes cost data, quality data, and patient experience data.

Figure 15:
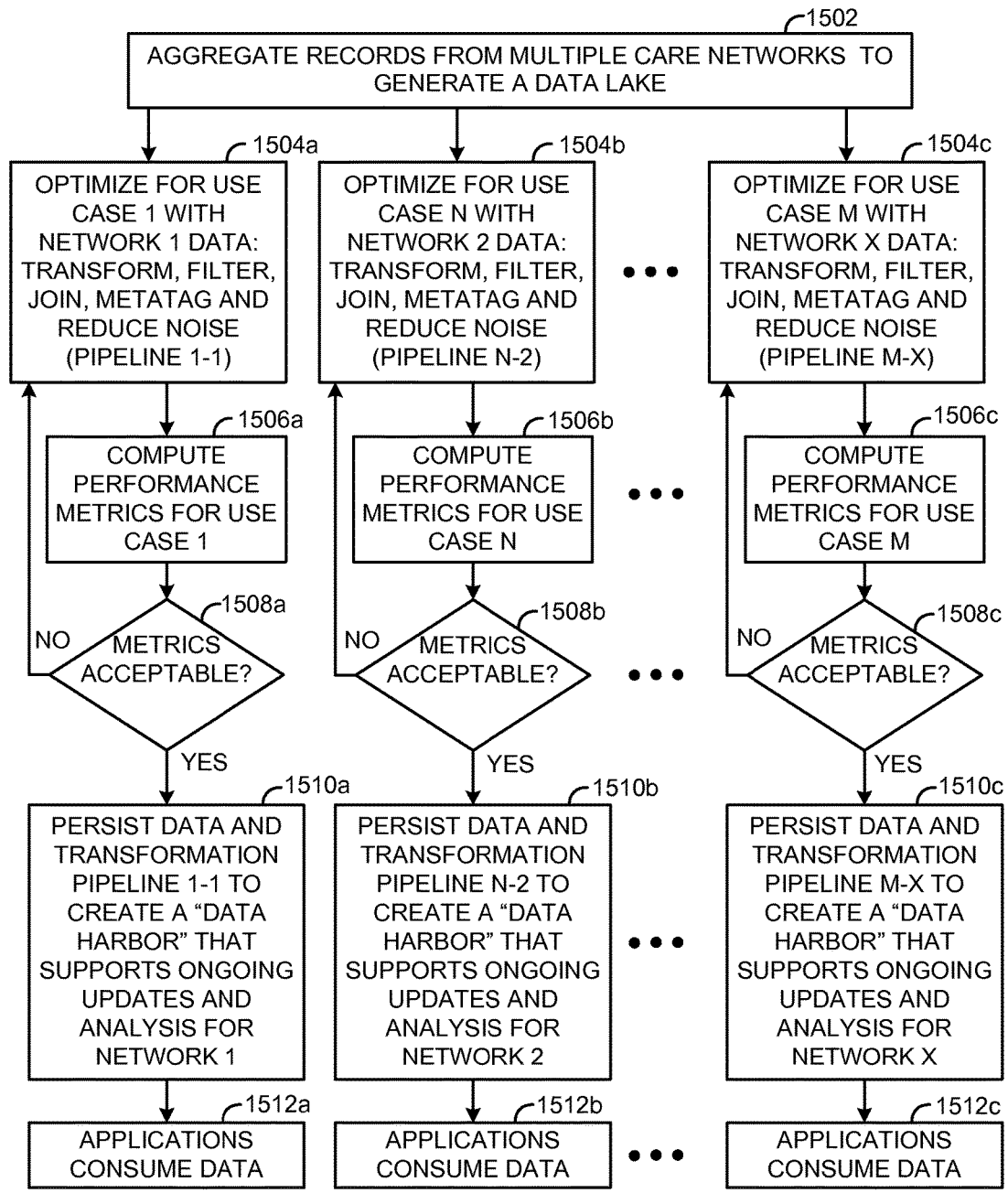
FIG. 15 is a flow chart for the parallel processes of tailored data usage, in accordance with an embodiment.

Turning now to FIG. 15 the presently disclosed systems and methods may be applied beyond a single referral network to enable the analysis of millions of patient records. This degree of referral analysis may elucidate behavioral patterns for patients, such as when patients influence referral activity (and the degree of such influence). These behavioral patters, and particularly patient influence factors, may be utilized by health networks to rebuild their database structures to analyze among their entire patient cohort for a specific purpose, as defined by the health network. Currently, database analysis for a health network is limited to applying an existing schema. Generally, this schema may provide insights into the health network's patient cohort, but may be limited due to the inability to customize the database for a particular issue or use case. Via this customization of the health network's database, nuances may be detected that may have otherwise not been available.

Such systems enable adding data into database (at 1502) in order to provide desired data on the fly. In big data analysis, this activity may be referred to as a data lake, or enterprise data hub. From the data lake, multiple parallel analyses may be performed for one or more health networks, and for one or more use cases per network. In the example flowchart, this is illustrated by the parallel processes depicted. High level process determines the question pertinent to the health network, then iterative queries determine the data relevant to the question. This includes transformation, filtering, joining, metatagging and noise reduction of the data to optimize it for each pertinent use case for each relevant network (at 1504a-1504c, respectively). Next, the system applies the data tuning to gauge performance metrics for the relevant use case (at 1506a-1506c, respectively). If the data tuning is found to be acceptable (at 1508a-1508c, respectively), then the tuning may be persisted and repeated for future analysis (at 1510a-1510c, respectively). This data persistence may be referred to as generating a "data harbor" that supports ongoing updates and analysis for the relevant network. Lastly, the data harbor may be consumed by applications for subsequent processes and analysis (at 1512a-1512c, respectively).

Figure 14A:
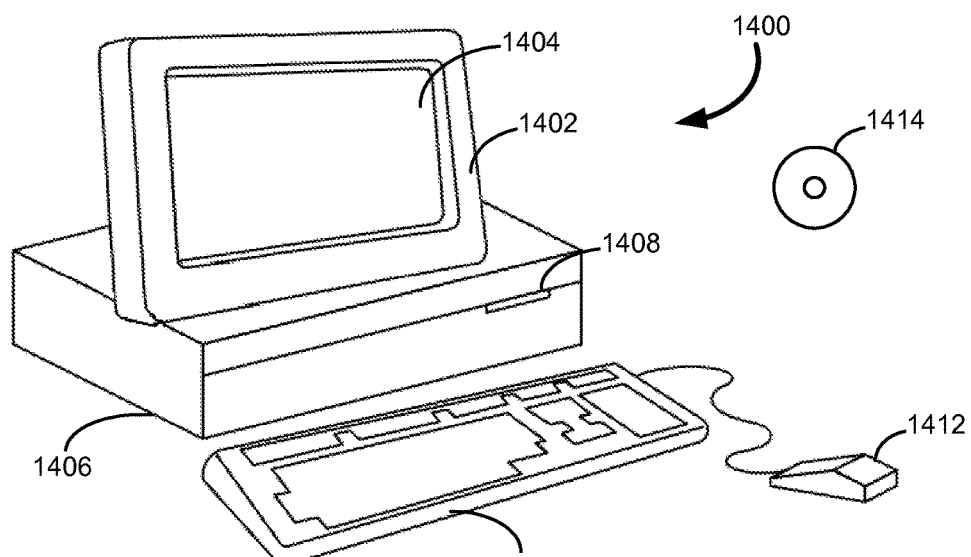
FIGS. 14A and 14B are example illustrations of a computer system capable of embodying the current invention.
Figure 14B:
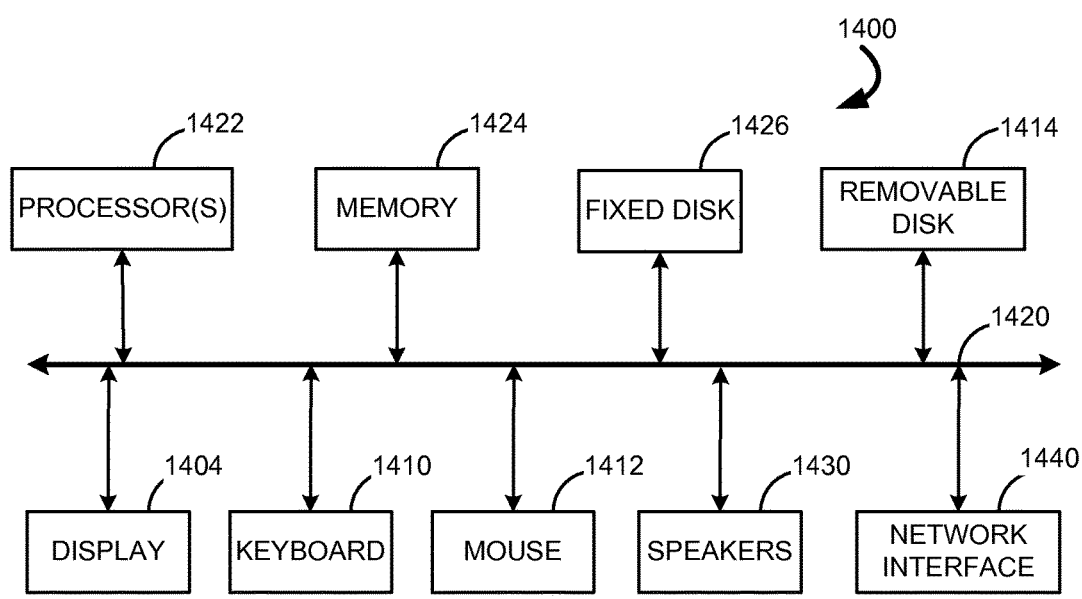

Now turning to FIGS. 14A and 14B, which illustrate a Computer System 1400, which is suitable for implementing embodiments of the present invention. FIG. 14A shows one possible physical form of the Computer System 1400. Of course, the Computer System 1400 may have many physical forms ranging from a printed circuit board, an integrated circuit, and a small handheld device up to a huge super computer. Computer system 1400 may include a Monitor 1402, a Display 1404, a Housing 1406, a Disk Drive 1408, a Keyboard 1410, and a Mouse 1412. Disk 1414 is a computer-readable medium used to transfer data to and from Computer System 1400.

FIG. 14B is an example of a block diagram for Computer System 1400. Attached to System Bus 1420 are a wide variety of subsystems. Processor(s) 1422 (also referred to as central processing units, or CPUs) are coupled to storage devices, including Memory 1424. Memory 1424 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A Fixed Disk 1426 may also be coupled bi-directionally to the Processor 1422; it provides additional data storage capacity and may also include any of the computer-readable media described below. Fixed Disk 1426 may be used to store programs, data, and the like and is typically a secondary storage medium (such as a hard disk) that is slower than primary storage. It will be appreciated that the information retained within Fixed Disk 1426 may, in appropriate cases, be incorporated in standard fashion as virtual memory in Memory 1424. Removable Disk 1414 may take the form of any of the computer-readable media described below.

Processor 1422 is also coupled to a variety of input/output devices, such as Display 1404, Keyboard 1410, Mouse 1412 and Speakers 1430. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, motion sensors, brain wave readers, or other computers. Processor 1422 optionally may be coupled to another computer or telecommunications network using Network Interface 1440. With such a Network Interface 1440, it is contemplated that the Processor 1422 might receive information from the network, or might output information to the network in the course of performing the above-described referral analysis. Furthermore, method embodiments of the present invention may execute solely upon Processor 1422 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. In a health information management system, a method executed on a computer processor for referral analysis, the method comprising:
    aggregating data from multiple health networks into a consolidated data lake;
    meta tagging data from the data lake for a unique health network and use case at each processing units of a plurality of parallel processing units;
    generating separate data harbors for each health network from the meta tagged data;
    identifying, by the computer processor using a data harbor associated with a given health network, explicit referral activity reported into a referral workflow system;
    inferring referral activity, by the computer processor, not reported into the referral workflow system by:
        collecting medical records from the data harbors;
        identifying terms in a first set of the medical records that indicate a medical event through conceptual models using machine learning;
        determining when the medical event is a severe condition based upon rules;
        determining a suggested event based upon the conceptual models for the severe condition;
        identifying if terms in a second set of the medical records that are after the first set of the medical records indicate a referral event matching the suggested event; otherwise
        determining that no referral event occurred;
    generating reporting metrics, by the computer processor, from the inferred and explicit referral activity;
    generating a referral suggestion, by the computer processor, by identifying a condition, activity, procedure, or diagnosis for the referral, selecting physicians within a geographic area who are properly specialized for the condition, activity, procedure, or diagnosis, and filtering the physicians by at least one of patient preferences, default preferences, referring physician history, quality of treatment, and network preferences; and
    displaying the referral suggestion to a patient via a web portal on a computing device.

2. The method of claim 1 wherein the intent-based clustering of medical information further comprises:
    reconciling the medical information; and
    clustering the reconciled medical information, wherein the clustering includes applying at least one clustering rule to the reconciled medication information.

3. The method of claim 2 wherein the reconciling further comprises applying at least one similarity rule.

4. The method of claim 3 wherein the at least one similarity rule includes comparing patient data attributes.

5. The method of claim 4 further comprising computing a distance between the patient data attributes and clustered reconciled medical information.

6. The method of claim 5 wherein if the distance is less than a threshold, then the clustered reconciled medical information is included as a referral.

7. The method of claim 1 further comprising:
    aggregating patient health records from across multiple health networks into a data lake;
    designating a question of value for a health network;
    iteratively querying the data lake to determine data relevant to the question;
    including the relevant data in an analysis to determine performance gains.

8. A health information management system, including non-volatile machine readable data being executed on a processor, comprising:
    a data manager comprising a processor for aggregating data from multiple health networks into a consolidated data lake;
    separate parallel processing units comprising a processor for meta tagging data from the data lake for a unique health network and use case at each processing unit a plurality of data bases comprising a processor for generating separate data harbors for each health network from the meta tagged data;
    a referral collector comprising a processor executing the non-volatile machine readable data, configured to identify explicit referral activity reported into a referral workflow system using a data harbor associated with a given health network;
    an inference engine comprising a computer system executing the non-volatile machine readable data configured to infer referral activity not reported into the referral workflow system by:
        collecting medical records from the data harbors;
        identifying terms in a first set of the medical records that indicate a medical event through conceptual models using machine learning;
        determining when the medical event is a severe condition based upon rules;
        determining a suggested event based upon the conceptual models for the severe condition;
        identifying if terms in a second set of the medical records that are after the first set of the medical records indicate a referral event matching the suggested event; otherwise determining that no referral event occurred;

an analyzer comprising a computer system executing the non-volatile machine readable data configured to generate reporting metrics from the inferred and explicit referral activity;

the analyzer further configured to generate a referral suggestion by identifying a condition, activity, procedure, or diagnosis for the referral, selecting physicians within a geographic area who are properly specialized for the condition, activity, procedure, or diagnosis, and filtering the physicians by at least one of patient preferences, default preferences, referring physician history, quality of treatment, and network preferences; and an interface comprising a web portal on a computing device for displaying the referral suggestion to a patient.

9. The health information management system of claim 8 wherein the inference engine further comprises:

a reconciliation engine configured to reconcile the medical information; and an intent-based presentation engine configured to cluster the reconciled medical information, wherein the clustering includes applying at least one clustering rule to the reconciled medication information.

10. The health information management system of claim 9 wherein the reconciling further comprises applying at least one similarity rule.

11. The health information management system of claim 10 wherein the at least one similarity rule includes comparing patient data attributes.

12. The health information management system of claim 11 wherein the intent-based presentation engine is further configured to compute a distance between the patient data attributes and clustered reconciled medical information.

13. The health information management system of claim 12 wherein if the distance is less than a threshold, then the clustered reconciled medical information is included in a presentation cluster prepared for the user.

14. The health information management system of claim 8 further comprising a big data analyzer configured to perform the steps of:

aggregating patient health records from across multiple health networks into a data lake;

designating a question of value for a health network;

iteratively querying the data lake to determine data relevant to the question;

including the relevant data in an analysis to determine performance gains.

* * * * *